United States Patent [19]

Lee, Jr. et al.

[11] 4,058,442

[45] Nov. 15, 1977

[54] PHOTOPOLYMERIZABLE COMPOSITION FOR FORMED-IN-PLACE ARTIFICIAL NAILS

[75] Inventors: Henry L. Lee, Jr., Pasadena; Jan A. Orlowski; Carl H. Fromm, both of Altadena, all of Calif.

[73] Assignee: Lee Pharmaceuticals, South El Monte, Calif.

[21] Appl. No.: 613,287

[22] Filed: Sept. 15, 1975

[51] Int. Cl.$^2$ .......................... C08L 1/32; C08F 2/46; C08F 8/00

[52] U.S. Cl. .......................... 204/159.12; 204/159.13; 204/159.15; 204/159.16; 260/879; 260/880 B; 424/61; 427/2; 427/4; 427/44; 427/53; 427/54

[58] Field of Search .................. 204/159.12, 159.13, 204/159.15, 159.16; 427/2, 4, 44, 54, 53; 424/61; 260/17 R, 17 A, 880 B, 879; 106/183, 180

[56] References Cited

U.S. PATENT DOCUMENTS

| | | | |
|---|---|---|---|
| 3,709,866 | 1/1973 | Waller | 204/159.23 |
| 3,756,827 | 9/1973 | Chang | 96/86 P |
| 3,809,569 | 5/1974 | Aronoff et al. | 204/159.23 |
| 3,862,021 | 1/1975 | Hagihara et al. | 204/159.15 |
| 3,883,453 | 5/1975 | Takahashi et al. | 260/15 |
| 3,896,014 | 7/1975 | Rosenberg | 204/159.23 |
| 3,912,670 | 10/1975 | Huemmer et al. | 204/159.15 X |
| 3,927,203 | 12/1975 | Seymour et al. | 424/61 |
| 3,950,238 | 4/1976 | Eldred | 204/159.15 |
| 3,996,394 | 12/1976 | Harris | 427/54 |
| 3,998,712 | 12/1976 | Hickmann et al. | 204/159.15 |

*Primary Examiner*—Murray Tillman
*Assistant Examiner*—Thurman K. Page

[57] ABSTRACT

Photopolymerizable composition of matter for the production of formed-in-place artificial nails.

16 Claims, No Drawings

PHOTOPOLYMERIZABLE COMPOSITION FOR FORMED-IN-PLACE ARTIFICIAL NAILS

BACKGROUND OF THE INVENTION

The invention relates to photopolymerizable compositions of matter for application to human nails to provide formed-in-place artificial nails.

Polymerizable compositions of matter for various dental and medical uses are known in the prior art. See generally U.S. Pats. Nos. 3,066,112; 3,179,623; 3,539,533; and 3,751,399. The prior art also suggests the use of photopolymerizable compositions for use in restorative dentistry. See e.g., U.S. Pat. No. 3,709,866.

Polymerizable compositions formulated for use in dentistry must satisfy a combination of rigorus criteria imposed by the conditions which exist in the mouth and to which such compositions are subjected in the course of mastication. Polymerizable dental restorative compositions must strongly adhere to tooth enamel, the hardest substance in the body. Such products must cure or set rapidly with only moderate exotherm. The cured product must be long lasting and hence characterized by high compressive strength, high modulus of elasticity in compression, flexure and tension, excellent wear resistance, excellent resistance to the effects of water, including hydrolysis. In general, these essential properties of polymerizable compositions for dental application are afforded by the selection of monomers to provide a low oxygen to carbon ratio and a high cross-link density and by the use, in combinaton with the selected monomers of particulate, usually mineral, fillers such as finely divided silica. These various ingredients are combined in proportion and in such manner as to provide a combination of properties in both the uncured and cured state effective to render the compositions useful for dental purposes.

Polymerizable compositions for the production of formed-in-place artificial nails must satisfy a different set of conditions and hence must demonstrate a different combination of uncured and cured properties.

Artificial fingernals must adhere, not to tooth enamel but to natural nails composed essentialy of keratin, which is a protein. The adhesion characteristics must be such that the artificial nail can be readily removed at any time it is desired to do so. Whereas dental restorative compositions must remain in place for years, artificial fingernails are normally replaced or removed after a few days or weeks The environment to which an artificial nail is subject in use is markedly different from that of the mouth. Whereas dental compositions must resist the effects of water, it is desirable that artificial fingernails soften in water in a manner similar to natural nails. Artificial nails, in contrast to dental restorative compositions, are subjected to repeated flexing and shearing forces and hence should not crack or break under such normal conditions of use. Desirably, artificial nails should be translucent, though opaque nails are usable in instances where they are to be coated with fingernail polishes or enamels.

The consistency in the uncured state is of particular importance in artificial fingernail compositions. In use, such compositions are applied to a substrate which includes the natural nail and an extension thereof in the form of an appropriately shaped, sheet-like material to which the artificial nail composition does not adhere. The artificial nail composition must accordingly be of such consistency as to permit ready application without undue flowing or dripping, must be readily deformable yet shape retentive and must provide a smooth, attractive surface appearance.

Commercially available artificial fingernail compositions are composed of separately packaged liquid monomer and particulate catalyst components. The monomer component package may also include accelerators, thickeners, plasticizers, dyes and other ingredients. The catalyst component package may also include additional ingredients such as fillers, opacifiers and dyes.

Polymerization or curing occurs only upon mixture of the contents of the two packages. The polymerization time is determined by the mass rstio of the monomer and filler which results from the initial mixing. The concentration of the solid filler phase at the outset of polymerization controls the flexural strength, flexural modulus and impact resistance of the polymerized matrix. The initial concentration of the solid filler phase depends, in turn, on the initial filler/resin ratio, the solubility rate of the filler in the resin, and the time available for the filler to dissolve.

With respect to any given two-package products, the solubility rate of the filler in the resin is fixed; hence variation in initial filler/resin ratio will result in significant differences in the mechanical characteristics of the resulting artificial fingernail or cured matrix.

Two-package artificial fingernail formulations are conventionally applied by dipping a brush first in the liquid monomer component and then into the powder component, including the filler and the catalyst. With this procedure, control of the monomer/filler ratio is difficult. Polymerization times and the mechanical characteristics of the cured fingernail are subject to significant erratic variations.

The variance in filler/resin ratio invariably consequent from the conventional use of such two-package formulations also results in varying mixture consistencies.

Long practice with such two-package compositions is routinely required even for a skilled operator to establish a technique effective to provide the generally uniform mix consistency which is desirable for the smooth application of the formulation requisite to provide a satisfactory artificial fingernail. In addition, such two-package, chemically-curing systems afford only limited application time. On the average only from two to four minutes are available in which to build and shape an artificial nail before the mixture becomes unmanageable due to the onset of curing.

The consequence is an uneconomical initial waste of material and the practical limitation of the use of artificial fingernails to professional manicurists.

Presently available artificial fingernail formulations including methylmethacrylate or ethylmethacrylate monomer irritate and sensitize skin and are dermatologically unacceptable. The substitution of other monomers for methyl- or ethylmethacrylate has resulted in unsatisfactory artificial nails which lack a hard-cured surface due to oxygen inhibition of polymerization.

Attempts to replace methyl- or ethylmethacrylate have focused on acrylate or methacrylate monomers of higher molecular weight. Biologically acceptable monomers of this type, e.g., acrylic esters which include large or high molecular weight alcohol radicals yield artificial fingernals which are brittle and hence crack or break. Such artificial nails, moreover, become increasingly brittle with age. This problem is not satisfactorily solved by the use of conventional plasticizers such as dibutyl phthalate. Such plasticizers, when used in effective amounts, tend to weaken the artificial nail, impair its resistance to organic solvents, impair its adhesion to the natural nails, and in some cases to introduce new biological and dermatological problems.

These various problems which attend self-cured, two-packaged artificial fingernail compositions are largely alleviated by the single package, photopolymerizable compositions of this invention.

THE INVENTION

This invention provides a photopolymerizable composition for the production of artificial nails which, in the uncured state, can readily be smoothed and shaped before polymerization is initiated, and which, after curing, demonstrates excellent physical properties and appropriate adhesion to natural nails and can be shaped with conventional fingernail filing implements in the same manner as natural nails.

In accordance with the invention, there is provided a photopolymerizable composition for the producton of artificial nails by direct application to human nails which comprises a mixture of (i) from about 40% to about 90% by weight of a monomer selected from the group consisting of the methyl, ethyl, propyl, isopropyl, butyl, isobutyl, furfuryl, tetrahydrofurfuryl and glycidyl esters of acrylic and the alkyl substituted acrylic acids in which the alkyl groups have from 1 to 4 carbon atoms, (ii) from about 3 to about 40% by weight of a monomer selected from the group consisting of the esters of polyhydric alcohols having from two to about four hydroxyl groups with acrylic acid and the alkyl substituted acrylic acids in which the alkyl groups have from one to four carbon atoms, (iii) from about 0.1 to about 30% by weight of a photopolymerization initiator, and (iv) from about 5% to about 25% by weight of a modifier which is soluble or swellable in the mixture and acts to improve consistency and flexural properties. The modifier is either a particulate cured elastomer, or a mixture of particulate cured elastomer and particulate cellulose ester of ether-ester in at least 4.5:1 weight ratio. If added as a cured elastomer, the modifier may be of a particle size up to about 300 microns. In the uncured state the compositions of this invention have a consistency of from 5 to 3000 seconds. In the cured state, these compositions exhibit a flexural modulus of elasticity of at least $50 \times 10^3$ psi, a flexural strength of at least 3000 psi, and an elongation to break under flexural stress of at least 3.5%. Such compositions of the invention provide artificial fingernails which exhibit excellent translucency and adhesion to natural nails in vivo and hence of long life. In actual tests, they are non-sensitizing to humans.

MEASUREMENT OF PHYSICAL PROPERTIES

The various physical properties by which the compositions of this invention are characterized are determined and measured in the manner hereinafter described:

1. Consistency

Consistency was characterized using a sphere immersion technique consisting of measuring the time it takes for a smooth glass sphere have a diameter of 0.875 inches and a density of 2.14 g/cm³ to submerge completely in the test medium, following the release of the sphere from the position where the sphere just touches the surface of the medium. Because of their thixotropic character, the materials tested were allowed to reach equilibrium in a non-agitated state for a period of 3 hours prior to testing at a stabilized room temperature of 23 ± 1° C. In each case the test medium was protected from ultraviolet exposure to insure that no curing occurred. This method is closely related to Federal Test Method Std. No. 4272, May 15, 1958.

2. Flexural Modulus of Elasticity, Flexural Strength and Elongation to Break under Flexural Strength Transverse Beam Bending The transverse bending beam test is used to provide the data for calculation of flexural modulus of elasticity, flexural strength and flexural elongation to break.

a. Sample Preparation

An artificial fingernail material was cured in an aluminum circular mold of 2 inches diameter and 0.04 inch thickness. The curing was effected using 4500μW/cm² ultraviolet irradiation intensity at the surface of material for a period of 12 minutes. The cured disc was removed from the mold, inspected for air-bubble entrapment and then cut in half, using a high-speed dental lathe. A rectangular sample (0.25 inch wide by 0.04 inch thick by 1.25 inches long) was thereupon obtained from each half of the disc by grinding on a circular grinder using waterproof silicon carbide No. 180 paper in a previously outlined contour of the defined dimensions. The sample dimensions were then measured and the values recorded to 0.001 inch. The dimensions varied within 0.01 inch in width, 0.004 in thickness and 0.05 inch in length. The samples thus prepared were aged for 24 ± 2 hours in the dark at 37° C in an air oven prior to testing. A minimum of four samples was prepared for each material and tested.

b. Testing

The testing was performed using an Instron machine, Mod. TT-C with automatic load-deflection recording,.

The dimensions of sample supports and load-head were the same as in ADA Spec. No. 12 (Guide to Dental Materials and Devices, p. 207, FIGS. 12-4, 7th edition, ADA 1974–75). The load-head speed was 0.2 inches/min. for all the specimens tested.

c. Load-Deflection Curve — Data Manipulation*

The point at which the load-deflection curve loses its initial linearity was defined as the yield point. The values of load and deflection taken at the yield point were used to calculate the flexural modulus of elasticity, using the equation:

$$E \text{ (psi)} = \frac{Flo^3}{4cd^3Y}$$

where: F = load in lbs at yield point
Lo = length between sample supports, in inches
c = sample width, in inches
d = sample thickness, in inches
Y = vertical deflection at yield point, in inches

*See: Mechanical Properties of Polymers and Composites, Vol. 1, Lawrence E. Nielsen. Published by Marcel Dekker, Inc., New York, 1974.

The point on the load deflection curve characterized by the maximum load applied before either rupture or cold-flow condition occurred was used to calculate the flexural strength, using the equation:

$$\sigma \text{ max (psi)} = \frac{3Flo}{2cd^2Y}$$

where: Y = deflection of maximum load, inch
d, Lo - as defined above

3. Translucency

Cured chips of artificial fingernail material were cured in an aluminum circular mold of 2 inches diameter and 0.04 inch thickness. These chips were then observed in a Bausch and Lamb Spectrometer 20 equipped with reflectance chamber against a black backing, using as control a magnesium oxide sample of reflectance 80% which is essentially transparent, i.e., approaches 100% translucency, being comparable to glass in this respect.

4. Adhesion to Natural Nails

To measure adhesion, it is necessary to provide a handle or prong to which tension means can be secured for applying the tension needed to test the adhesive joint. Initial attempts to test such joints in vitro on human nail tissue were impeded by the difficulty of providing such nails with a stable subsurface. Vertically a system was worked out in which a ⅛ by ⅛ inch section of such natural nail was placed in the horizontal trapezoidal undercut of a ⅜ inch steel screw of essentially trapezoidal cross-section and the entire assembly embedded in fast-curing epoxy resin in a manner such that care was taken to leave the outer, convex surface of the nail free. An attempt to then form an adhesive joint of artificial fingernail composition of this invention because the nail surfaces of two such assemblies was abortive because the surface thereby rendered available for exposure to ultraviolet radiation was too thin to permit curing. Tests were accordingly conducted using compositions of this invention from which the photoinitator was omitted and to which a conventional benzoyl peroxide-tertiary amine curing system was added.

After chemical curing of the junctions between the assemblies, they were aged for 24 hours in the dark at 37° C in an air oven and subjected to tensile testing on the Instron apparatus Model TT-C at X-head speed of 0.02 inches/minute.

The results of these tests, were considered conjunctively with clinical tests on human subjects demonstrating that otherwise identical formulations (i) cured chemically and (ii) cured with ultraviolet irradiation, showed consistently longer life for the adhesive bond of the ultraviolet cured systems and it was concluded that the adhesion values for otherwise identical ultraviolet cured compositions would exceed those measured in the tests.

In a further effort to obtain direct measured adhesion values for the compositions of this invention, an "in vivo' test was devised in which metal hooks were imbedded in the artificial nail compositions placed directly on nails of living subjects. Again, the compositions could not be cured under ultraviolet light because the surface available for exposure to the light was shadowed by the hooks. Accordingly, the test was run with otherwise identical chemically cured formulations. The samples were allowed to age for 24 ± 2 hours after curing, vertical force was applied to the hooks and the force needed to break the adhesive junction was measured with a calibrated spring. The values obtained were lower by an order of magnitude of approximately 10 times than those obtained in the above described in vitro test. The difference is attributed mainly to the higher moisture and oil content of in vivo nails and to such effects as may be consequent from proximity of the human bloodstream to the nail tissue and only secondarily to differences in the test method per se. The in vivo results are believed to be more consistent with reality.

PERMISSIBLE VARIATIONS OF THE INVENTION

The compositions of this invention have an uncured consistency of from 5 to 3000 seconds; preferably 1000 to 2500 seconds; and, after curing, a flexural modulus of elasticity of at least $50 \times 10^3$, preferably from $150 \times 10^3$ to about $300 \times 10^3$, a flexural strength of at least 3000 psi, preferably from about 5000 to about 10,000 psi; an elongation to break under flexural stress of at least 3.5%; preferably from about 5% to about 7%, an in vivo adhesion to natural nails of at least 25 psi and preferably from about 30 to about 200 psi, and a translucency of about 50–75%, preferably about 65–75%. The in vitro adhesion of otherwise identical chemically cured compositions, measured as described, is in the range of 300 to 1400 psi.

The polymerizable monomers comprising about 40 to 90% by weight of the uncured composition may be prepared by esterifying acrylic acid, methacrylic acid, ethyl acrylic acid, n-propyl acrylic acid, isopropyl acrylic acid, n-butyl acrylic acid, isobutyl acrylic acid or tertiary butyl acrylic acid with methyl, ethyl, propyl, isopropyl, butyl, isobutyl, furfuryl, tetrahydrofurfuryl or glycidyl alcohols. Mixtures of esters so prepared may also comprise 40–90% of the composition. The monomers comprising 3–40% by weight and preferably about 3 to 10% by weight of composition may be prepared by esterifying any of the above-named acids with any polyhydric alcohol having 2 to 4 hydroxy groups including diethylene glycol, triethylene glycol, tetraethylene glycol, glycerol, 1,3,3-trimethylol propane, 1,6 hexanediol, 1,4 butene-2-diol, 1,2 phenylene glycol, 1,4 phenylene glycol, 1,3 phenylene glycol, 2,2-bis [4(2,3 dihydroxypropoxyl)phenyl] propane, 2,2 bis[4(2-hydroxyethoxy) phenol] propane, and many others which will readily occur to those skilled in the art. Diethylene glycol is preferred. These latter monomers act at least in part as cross-linking agents in the curing step.

The monohydric alcohol acylic ester monomer constitutes from about 40% to about 90%, preferably about 70 to about 80% of the composition. The polyhydric alcohol monomer constitutes from about 3 to about 40%, preferably about 3% to about 10% by weight of the composition.

Any photoinitiator effective to initiate polymerization of the monomer mixture upon exposure to long-wave ultraviolet radiation, i.e., approximately 280 to 340 rm can be utilized. Initiators disclosed in the prior art include benzoin methyl ether, benzoin and various benzoin derivatives. See, e.g., U.S. Pat. No. 2,367,661 and the article entitled Aromatic Keto Compounds as Initiators in Photopolymerizations, Heine et al. Angew Chem Int'l, Ed. 11, 974 (1972). Care must be exercised however, to select an initiator which is not dermatologically objectionable.

A preferred class of initiators are dioxolane compounds having the formula:

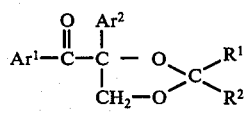

in which $R^1$ and $R^2$ are H or any organic radical having a molecular weight of 210 or less and $Ar^1$ and $Ar^2$ are selected from phenyl, naphthyl and non-sterically hindered substituted phenyl or naphthyl radicals in which the substituents each have a molecular weight of 210 or less.

Of this class the compounds

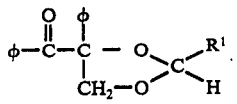

where $R^1$ is phenyl or methyl, and

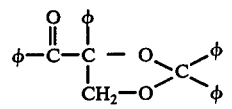

are particularly preferred.

This class of photoinitiators is the subject matter of copending Brattesani Application Ser. No. 613,286 filed Sept. 15, 1975, the disclosure of which is incorporated herein by reference.

The photoinitiator is present in a small but effective amount, generally from about 0.1 to about 30%, and preferably from about 0.2% to about 5% by weight of the composition.

The modifier ingredient is soluble or at least swellable in the mix, is a solid elastomer and is added to the composition in particulate form, the particle size being below about 300 microns to insure ready compatability with the mix.

Typical elastomers which are suitable include carboxy terminated butadiene acrylonitrile copolymers; methacrylate modified butadiene styrene block copolymers of approximately 1:1:1 monomer ratio; butadiene-styrene-acrylonitrile copolymers, carboxy terminated polyisobutylenes*, etc. Other suitable elastomers will be apparent to those skilled in the art.

*See generally Drake and Siebert "Elastomer-Modified Epoxy Resins for Structural Applications" prepared for 20th National SAMPE Symposium and Exhibition. Apr. 29, 30 and May 1, 1975. San Diego, California.

A preferred elastomer is understood to be a methacrylate modified butadiene sytrene block copolymer sold under the tradename "Blendex BTA III's" by Borg-Warner Corporation, Parkersburg, West Virginia 26101.

The modifier may also be composed partially of particulate cellulose esters and ether-esters such as cellulose acetate, cellulose acetate butyrate, cellulose propionate, cellulose butyrate, cellulose acetate propionate, acetoxymethyl cellulose, cellulose glycollate, etc.

The modifier constitutes about 5-25% by weight of the composition and preferably 12-18% by weight.

Preferably, the modifier will consist entirely of elastomer. If cellulose ester of ether ester is added, the weight ratio of elastomer to resin should be at least about 4.5:1. In the particularly preferred embodiments, the modifier consists entirely of an elastomeric material.

Optionally, the compositions of the invention may also contain mineral fillers such as finely divided quartz or colloidal silica which act as thixotroping agents. Such mineral fillers may constitute from about 2 to about 10% by weight of the composition, preferably 3 to 5%. Their average particle size is from below 1 micron in the case of colloidal silica to not more than about 60 microns.

The compositions of the invention may also optionally contain such additives as dyes, antioxidants, conventional solvent type plasticizers, e.g., phthalate esters, opacifiers such as $TiO_2$ or an alkyl polysiloxane, conventional dispersing agents for dyes, etc., in amounts not aggregating more than 10% by weight of the composition and preferably not more than 2-5%.

EXAMPLE I a. The following illustrates a composition according to the invention. The ingredients were blended in the proportions indicated:

| Ingredients | % by Weight |
| --- | --- |
| Tetrahydrofurfuryl Methacrylate | 73.32 |
| Diethylene Glycol Dimethacrylate | 8.15 |
| 3-benzoyl-1,3-diphenyl dioxolane | 0.40 |
| Cellulose Acetate Butyrate | 2.24 |
| Particulate Block Copolymer of Styrene, Butadiene and Methacrylate, 1:1:1 Monomer Ratio | 13.85 |
| Dimethylpolysiloxane (Opacifier) | 2.04 |
| Pink Dye | $0.2 \times 10^{-6}$ |

The blended composition is paste-like and has a consistency of 1700 seconds. It was readily applicable to natural nails, and could be used to form an extension beyond the tip of the natural nail if a form such as those described generally in U.S. Pat. Nos. 2,779,283 or 3,157,912 was used. When cured in five minutes by exposure to ultraviolet light of wavelength 300-400 nm and an intensity of about $8000\mu W/cm$, the artificial fingernail composition exhibited the following properties:

| | |
| --- | --- |
| Flexural modulus of elasticity | $162.6 \times 10^3$ psi |
| Flexural strength | 5850 psi |
| Flexural elongation to break | 5.34% |
| In vivo adhesion to natural nails | exceeding 56 psi |

The formulation was tested on at least 300 human subjects with no dermatological irritation or sensitization being manifested. The minimum life of the nails in these tests was two weeks, and no failures of the adhesive bond were observed in any of these tests. The nails also exhibited excellent crack resistance b. The following example, identical to Example 1(a) except for omission of elastomer particles illustrates that the compositions without modifier are unsuitable for use as artificial fingernails. The ingredients were mixed in the proportions indicated:

| Ingredients | % by Weight |
| --- | --- |
| Tetrahydrofurfuryl Methacrylate | 85.10 |
| Diethylene Glycol Dimethacrylate | 9.46 |
| Cellulose Acetate Butyrate | 2.60 |
| Dimethylpolysiloxane | 2.37 |
| 3-Benzoyl-1,3-Diphenyl Dioxolane | 0.46 |
| Dyes | $0.2 \times 10^{-6}$ |

The uncured composition was a very thin watery liquid with a consistency of less than 1 second. It was not suitable for application to nails and could not be formed in the manner stated in Example 1.

When cured in the manner specified, it exhibited the following properties:

| | |
| --- | --- |
| Flexural modulus of elasticity | $448.4 \times 10^3$ psi |
| Flexural strength | 119,800 psi |
| Flexural elongation to break | 2.97% |

These properties, and the elongation to break under flexural stress, in particular, indicate a cured composition too brittle for successful use as artificial fingernails.

EXAMPLE II

The following ingredients were mixed in the proportions indicated:

| Ingredients | % by Weight |
| --- | --- |
| Tetrahydrofurfuryl Methacrylate | 75.02 |
| Diethylene Glycol Dimethacrylate | 8.34 |
| Particulate Block Copolymer of Styrene, Butadiene and Methacrylate, 1:1:1 Monomer Ratio | 11.61 |
| Cellulose Acetate Butyrate | 2.53 |
| Dimethylpolysiloxane | 2.08 |
| 3-benzoyl-1,3-diphenyl Dioxolane | 0.42 |
| Dyes | $0.15 \times 10^{-6}$ |

The consistency of the uncured mix was 1150 seconds.

The mixture was successfully coated on fingernails and formed as in Example 1(a). When cured as indicated, it exhibited the following properties:

| Flexural modulus of elasticity | $193 \times 10^3$ psi |
| --- | --- |
| Flexural strength | 7.57 psi |
| Flexural elongation to break | 5.30% |

Tests on 10 human subjects showed good general performance with no sensitization problems. Occasional cracking failures were observed at an earlier time than with the formulation of Example I.

We claim:

1. A composition that is readily applicable to human nails for cosmetic, protective and other purposes, and that polymerizes upon exposure to ultraviolet radiation, for the production of artificial nails by direct application to human nail tissue and curing by exposure to a controlled source of radiation, consisting essentially of, in admixture:
   i. from about 40% to about 90% by weight of the composition of a monofunctional ester monomer selected from the group consisting of esters of acrylic acid and 1–4 carbon alkyl-substituted acrylic acids with metyl, ethyl, propyl, isopropyl, butyl, isobutyl, furfuryl, tetrahydrofurfuryl and glycidyl alcohols, and mixtures of such esters;
   ii. from about 3% to about 40% by weight of the composition of an ester monomer selected from the group consisting of esters of acrylic acid and 1–4 carbon alkyl-substituted acrylic acids with polyhydric alcohols containing 2 to 4 hydroxyl groups and mixtures of such esters;
   iii. from about 0.1% to about 30% by weight of the composition of an initiator that acts upon exposure to ultraviolet radiation to initiate polymerization, and
   iv. from about 5% to about 25% by weight of the composition of a modifier that is soluble or swellable in the admixture and is selected from the group consisting of particulate cured elastomers up to 300 microns in particle size, and mixtures of such elastomers with a particulate cellulose ester or a particulate cellulose ether-ester having up to 300 micron particle size in the ratio of at least 4.5 parts by weight of the former to each one party by weight of the latter, said composition being characterized in that the composition after curing exhibits: an in vivo adhesion to natural human nails of at least about 25 pounds per square inch; a flexural modulus of elasticity of at least 50 × 10³ pounds/square inch; a flexural strength of at least 3000 pounds/square inch, and an elongation to break under flexural stress of at least 3.5% as measured under ambient pressure and temperature conditions.

2. A photopolymerizable composition according to claim 1 which also exhibits in its cured state a translucency of from about 50% to about 75%.

3. A composition in accordance with claim 1 that in its uncured state, ready for application to nails, is characterized by a consistency of from 5 to 3000 seconds as measured by a sphere immersion test in which the time is observed that is required for a smooth glass sphere having a diameter of 0.875 inches and a density of 2.14 g/cm³ to submerge completely in the composition, following release from a position in which the sphere just touches the surface of the composition.

4. A composition in accordance with claim 1 that also contains from about 2% to 10% by weight of a filler that is selected from the group consisting of colloidal silica and particulate mineral fillers having an average particle size of not more than about 60 microns.

5. A composition that is readily applicable to human nails for cosmetic, protective and other purposes, and that polymerizes upon exposure to ultraviolet light, for the production of artificial nails by direct application to human nail tissue and curing by exposure to a controlled source of ultraviolet light, consisting essentially of, in admixture:
   i. from about 70% to about 80% by weight of the composition of a monofunctional ester monomer selected from the group consisting of esters of acrylic acid and 1–4 carbon alkyl-substituted acrylic acids with methyl, ethyl, propyl, isopropyl, butyl, isobutyl, furfuryl, tetrahydrofurfuryl and glycidyl alcohols, and mixtures of such esters;
   ii. from about 3% to about 10% by weight of the composition of an ester monomer selected from the group consisting of esters of acrylic acid and 1–4 carbon alkyl-substituted acrylic acids with polyhydric alcohols containing 2 to 4 hydroxyl groups and mixtures of such esters;
   iii. from about 0.2% to about 5% by weight of the composition of an initiator that acts upon exposure to ultraviolet light to initiate polymerization, and
   iv. from about 12% to about 18% by weight of the composition of a modifier that is soluble or swellable in the admixture and is selected from the group consisting of particulate cured elastomers up to 300 microns in particle size, and mixtures of such elastomers with a particulate cellulose ester or a particulate cellulose ether-ester having up to 300 micron particle size in the ratio of at least 4.5 parts by weight of the former to each one part by weight of the latter, said composition being characterized in that the composition after curing exhibits a flexural modulus of elasticity of from about 150 × 10³ to about 300 × 10³ psi, a flexural strength of from about 5000 to about 10,000 psi, an elongation to break under flexural stress of from about 5% to 7% as measured under ambient pressure and temperature conditions, an in vivo adhesion to natural human nails of at least about 30 pounds per square inch, and a translucency of from about 75% to about 75%.

6. A composition in accordance with claim 5 that in its uncured state, ready for application to nails, is characterized by a consistency of from 1000 to 25000 seconds as measured by a sphere immersion test in which the time is observed that is required for a smooth glass sphere having a diameter of 0.875 inches and a density of 2.15 g/cm³ to submerge completely in the composition, following release from a position in which the sphere just touches the surface of the composition.

7. A composition in accordance with claim 5 in which component (iv) comprises at least 5 parts by weight of particulate methacrylate/butadiene/styrene block copolymer of generally 1:1:1 monomer ratio and not more than 1 part by weight of particulate cellulose acetate butyrate.

8. A composition in accordance with claim 5 comprising about 73% by weight tetrahydrofurfuryl methacrylate, about 8% by weight diethylene glycol dimethacrylate, and 0.4% by weight 3-benzoyl-1, 3-diephenyl dioxolane, about 14% by weight particulate block copolymer of methacrylate/styrene/butadiene in 1:1:1 monomer ratio, and about 2% by weight cellulose acetate butyrate.

9. A photopolymerizable composition according to claim 5 in which component (i) is tetrahydrofurfuryl methacrylate.

10. A photopolymerizable composition according to claim 5 in which component (ii) is diethylene glycol dimethacrylate.

11. A photopolymerizable composition according to claim 5 in which component (iii) is a compound of the formula

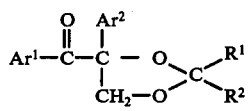

wherein R¹ and R² are selected from H and organic radicals having a molecular weight of not more than 210 and Ar¹ and Ar² are selected from the group consisting of phenyl, naphthyl and non-sterically hindered substituted phenyl and naphthyl rings wherein each substitutent has a molecular weight of not more than 210.

12. A photopolymerizable composition according to claim 11 in which Ar¹ and Ar², R¹ are each phenyl and R² is methyl.

13. A photopolymerizable composition according to clam 11 in which Ar¹, Ar² and R² are phenyl and R¹ is H.

14. A photopolymerizable composition according to claim 11 in which Ar¹, Ar² and R² are phenyl and R¹ is methyl.

15. A composition that is readily applicable to human nails for cosmetic, protective and other purposes, and that polymerizes upon exposure to actinic light, for the production of artificial nails by direct application to human nail tissue and curing by exposure to a controlled source of actinic light, consisting essentially of, in admixture:
i. from about 70% to about 80% by weight of the composition of the monofunctional ester monomer, tetrahydrofurfuryl methacrylate;
ii. from about 3% to about 10% by weight of the composition of the ester monomer, diethylene glycol dimethacrylate;
iii. from about 0.2% to about 5% by weight of the composition of an initiator that acts upon exposure to ultraviolet light to initiate polymerization, and
iv. from about 12% to about 18% by weight of the composition of a particulate cured elastomer that is soluble or swellable in the composition, the particles of which are up to 300 microns in particle size, said composition after curing exhibiting a flexural modulus of elasticity of from about 150 × 10³ to about 300 × 10³ psi, a flexural strength of from about 5000 to about 10,000 psi, an elongation to break under flexural stress of from about 5% to 7%, an in vivo adhesion to natural human nails of from about 3 psi to about 200 psi, and a translucency of from about 50% to about 75%; said composition in its uncured state, ready for application to nails, being characterized by a consistency of from 1000 to 2500 seconds as measured by a sphere immersion test in which the time is observed that is required for a smooth glass sphere having a diameter of 0.875 inches and a density of 2.14 g/cm³ to submerge completely in the composition, following release from a position in which the sphere just touches the surface of the composition.

16. A composition in accordance with claim 15 in which component (iii) is a compound of the formula

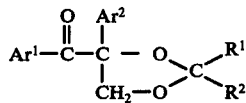

wherein R¹ and R² are selected from H and organic radicals having a molecular weight of not more than 210 and Ar¹ and Ar² are selected from the group consisting of phenyl, naphthyl, and non-sterically hindered substituted phenyl and naphthyl rings wherein each substituent has a molecular weight of not more than 210; and component (iv) is a particulate methacrylate/butadiene/styrene block copolymer of 1:1:1 monomer ratio.

* * * * *

UNITED STATES PATENT OFFICE
CERTIFICATE OF CORRECTION

Patent No. 4,058,442  Dated November 15, 1977

Inventor(s) Henry L. Lee, Jr., Jan A. Orlowski and Carl H. Fromm

It is certified that error appears in the above-identified patent and that said Letters Patent are hereby corrected as shown below:

Claim 1, col. 9, line 44, for "metyl" read "methyl"; line 65, for "party" read "part".

Claim 5, col. 10, line 67, for "75%" read "65%".

Claim 6, col. 11, line 3, for "25,000" read "2,500".

Signed and Sealed this

Twenty-first Day of March 1978

[SEAL]

Attest:

RUTH C. MASON  
Attesting Officer

LUTRELLE F. PARKER  
Acting Commissioner of Patents and Trademarks